United States Patent [19]

Poindexter

[11] Patent Number: 4,814,455
[45] Date of Patent: Mar. 21, 1989

[54] DIHYDRO-3,5-DICARBOXYLATES

[75] Inventor: Graham S. Poindexter, Evansville, Ind.

[73] Assignee: Bristol-Myers Company, New York, N.Y.

[21] Appl. No.: 852,856

[22] Filed: Apr. 16, 1986

[51] Int. Cl.[4] .......................................... C07D 401/12
[52] U.S. Cl. ..................................... 546/273; 546/321
[58] Field of Search ................ 546/321, 273; 514/339, 514/356

[56] References Cited

U.S. PATENT DOCUMENTS

| | | | |
|---|---|---|---|
| 3,485,847 | 12/1969 | Bossert et al. | 546/321 |
| 3,883,543 | 5/1975 | Bossert | 546/321 |
| 3,985,785 | 10/1976 | Edenhofer et al. | 558/446 |
| 4,423,052 | 12/1983 | Araki et al. | 546/321 |
| 4,578,395 | 3/1986 | Yamaguchi et al. | 546/321 |
| 4,622,332 | 11/1986 | Wehinger et al. | 546/321 |
| 4,672,071 | 6/1987 | Clark et al. | 546/321 |

FOREIGN PATENT DOCUMENTS

| | | |
|---|---|---|
| 0088903 | 9/1983 | European Pat. Off. . |
| 0094159 | 11/1983 | European Pat. Off. . |
| 0097821 | 1/1984 | European Pat. Off. . |
| 0145434 | 6/1985 | European Pat. Off. . |
| 3207982 | 9/1983 | Fed. Rep. of Germany ...... 546/321 |
| 2120668 | 12/1983 | United Kingdom ................ 546/321 |

OTHER PUBLICATIONS

Bossert, et al., "4-Aryldihydropyridines, A New Class of Highly Active Calcium Antagonists", *Angew. Chem., Int. Ed. Engl.* 20, (1981), pp. 762–769.
Schramm, et al., "Novel Dihydropyridines With Positive Inotropic Action Through Activation of CA[2+] Channels:, *Nature*, 30, (9 Jun. 1983), pp. 535–537.
Chem. Abstracts. 98, 107166j (1983).
Derwent Abstract 83-798692/43 (Japanese Patent J5,8157,785-A Yoshitomi Pharm. Ind. KK).
Derwent Abstract 86-008339/02 (West German Patent DE 3522-579-A Toyama Chem. KK).

*Primary Examiner*—Jane T. Fan
*Attorney, Agent, or Firm*—Robert H. Uloth

[57] ABSTRACT

A series of compounds of the 1,4-dihydropyridine class with a 3-carboxylate group linked to an alkyleneaminoalkylene heteroatom have been prepared possessing the general formula

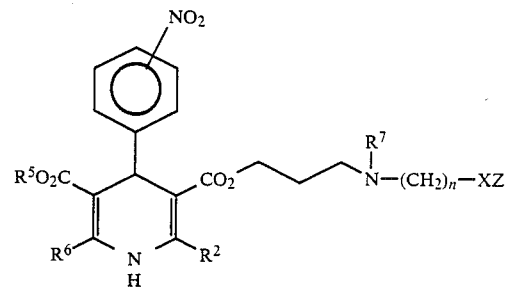

wherein $R^2$, $R^5$ and $R^6$ are independently selected from lower $(C_{1-4})$alkyl, hydroxy-lower-alkylene, lower alkoxy-lower-alkylene, lower alkylamino-lower-alkylene or lower dialkyl-amino-lower-alkylene; $R^7$ is selected from hydrogen, lower alkyl, phenyl-lower-alkylene, or phenylthio-lower-alkylene; n is the integer 2 or 3; X is a chemical bond, —O—, —S—,

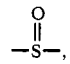

or —$NR^9$— wherein $R^9$ is hydrogen, lower alkyl, phenyl, or phenyl-lower-alkylene with the proviso that when X is a chemical bond, Z is a 3-indolyl ring; and Z is selected from the group consisting of phenyl substituted with 1 to 3 substituents independently chosen from among hydrogen, lower alkyl, or lower alkoxy, phenyl-lower-alkylene, or 3-indolyl.

Compounds of this series possess calcium channel blocking properties, afford protection against ischemia and inhibit aggregation of blood platelets.

1 Claim, No Drawings

DIHYDRO-3,5-DICARBOXYLATES

BACKGROUND OF THE INVENTION

The present invention concerns the heterocyclic carbon compounds of the 1,4-dihydropyridine class with a 3-carboxylate group linked to an alkyleneaminoalkyleneheteroatom group moiety. These compounds possess bio-affecting properties.

A substantial body of prior art has evolved over the last decade involving compounds of 4-aryl-1,4-dihydropyridine series which have calcium antagonist properties and are useful in the treatment of cardiovascular diseases. These calcium blocking effects appear to mediate vasodilation making these compounds useful in treating angina and hypertension. The archetypical compound of this series is nifedipine (formula 1):

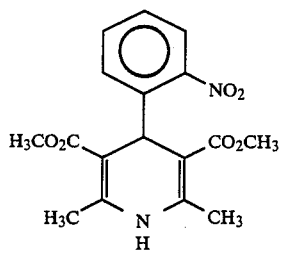

chemically, 4-(2'-nitrophenyl)-2,6-dimethyl-3,5-dicarbomethoxy-1,4-dihydropyridine. Nifedipine and some related 4-aryl-1,4-dihydropyridines are the subject of U.S. Pat. No. 3,485,847 issued Dec. 23, 1969. Numerous subsequent patents have been granted covering 1,4-dihydropyridines in which other substituent groups have been incorporated at the various ring positions of the dihydropyridine moiety via a diversity of chemical bonding groups. Many of the numerous reference patent documents directed to this class of compounds are distinguished by relatively minor structural changes in one or both of the carboxylate groups of the dihydropyridine nucleus.

U.S. Pat. No. 3,985,785 discloses the useful cardiovascular agent, Nicardipine (2), and related compounds.

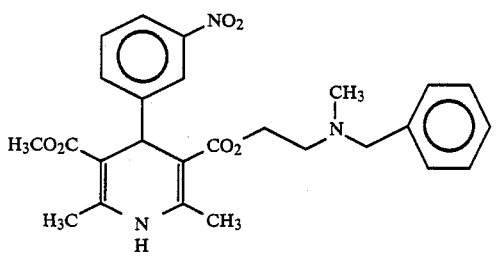

Other series of compounds related to Nicardipine may be generalized by the following structural formula (3)

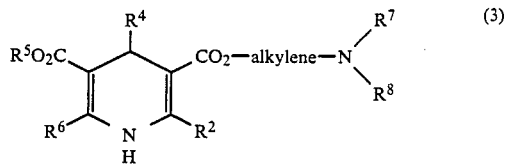

wherein $R^2$, $R^4$, $R^5$ and $R^6$ could be any of a number of substituent groups which have been repeatedly defined previously in the voluminous dihydropyridine literature; but with specific attention given to defining the substituent structure attached to the 3-position of the 1,4-dihydropyridine ring. The 3-position structural fragment comprises a secondary or tertiary amino function linked by means of an alkylene chain to the carboxylate group. The alkylene group, varying from 2 to 6 carbon atoms, can be straight chain or branched. In some instances, an aryl or hetaryl group is attached to the alkylene chain. For the two amino nitrogen substituents, $R^7$ is hydrogen or alkyl and $R^8$ can be alkyl, aralkyl, or aryl. The following references are representative of the art directed to Nicardipine-type compounds with a C-3 structural fragment of formula (4).

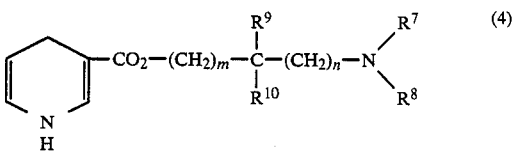

Araki, et al., U.S. Pat. No. 4,423,052 disclose compounds wherein m is 0, n is 1 or 2, $R^7$ and $R^8$ are alkyl or arylalkyl, $R^9$ is hydrogen and is aryl.

Similar compounds were disclosed in Chem. Abstracts, 98, 107166j (1983) wherein m is 0 to 3, n is 0 or 1, $R^7$ and $R^8$ are alkyl or aralkyl, $R^9$ is hydrogen and $R^{10}$ is aryl.

Compounds are disclosed in European patent application No. 128,010 in which m and n can be 0 to 6, $R^7$ and $R^9$ are alkyl, $R^8$ is optimally substituted aralkyl, and $R^{10}$ is hydrogen or alkyl.

In Japanese patent document No. J5 8,157,785A (abstract No. 83-798692/43) compounds were disclosed wherein m equals 0, n equals 1 or 2, $R^7$ and $R^8$ are alkyl, $R^9$ is hydrogen, and $R^{10}$ is a heterocyclic group.

Finally, patent applications have been published, e.g. DE No. 3522-579-A (abstract No. 86-008339/02); assigned to Toyama Chem. KK which disclose compounds where $R^7$ is

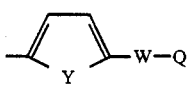

with Y being O, S or vinylene, W being O, S or alkylene, and Q being a nitrogen-containing heterocycle.

Of less relevance to the compounds of the instant invention would be those compounds which can be generalized by formula (5).

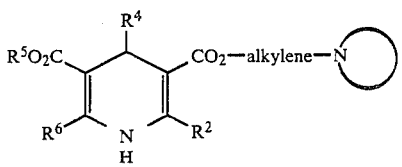

Compounds in this class are distinguished by the sidechain amino nitrogen atom being incorporated into a ring, generally of 5 to 7 members. In some instances, the ring may contain another heteroatom such as a nitrogen, e.g. a piperazine ring. Representative references for this type of dihydropyridine analog structure (5) would be the following:

European patent application No. 88,903-A (Yoshitomi Pharm. KK).

European patent application No. 94,159-A (Takeda Chem. Ind. Ltd.).

European patent application No. 97,821 (Pierrel SPA).

The compounds of the instant invention are distinguished over the art as they contain an additional aryl or hetaryl moiety, connected by a heteroatom and short alkylene chain to the amino nitrogen atom of the 3-carboxylate side chain. This particular structural elaboration, which is neither suggested nor made obvious by prior art, results in compounds which possess pharmacologic properties that would make them useful as cardiovascular agents. In essence, the instant compounds may be distinguished over compounds of the prior art both on the basis of molecular structure but also by biological action. While the instant compounds possess calcium channel blocking properties, as do the prior art compounds, the instant compounds have also been found to possess useful actions in protecting against ischemia and in inhibiting the aggregation of blood platelets. In summary, there is nothing in the prior art which anticipates or suggests the compounds of the instant invention.

SUMMARY AND DETAILED DESCRIPTION OF THE INVENTION

The present invention includes the compounds of Formula I and the acid addition salts of these substances.

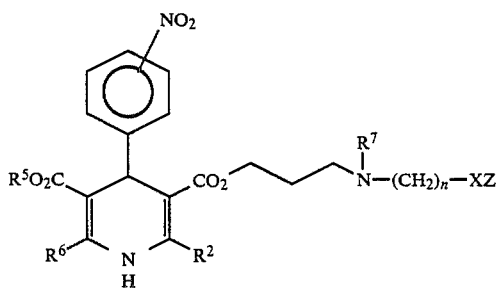

In the foregoing structural formula, the symbols $R^2$, $R^5$, $R^6$, $R^7$, n, X, and Z have the following meanings. $R^2$, $R^5$, and $R^6$ are independently selected from lower ($C_{1-4}$) alkyl, hydroxylower-alkylene, lower alkoxy-lower-alkylene, lower alkylamino-lower-alkylene, or lower dialkylamino-lower-alkylene and may be the same or different. The term "lower" used with alkyl, alkoxy or alkylene, etc. means that from 1 to 4 carbon atoms comprises the group. For example, lower alkoxy-loweralkylene refers to a $C_1$ to $C_4$ alkylene chain and a $C_1$ to $C_4$ alkyl group connected by an oxygen atom; similarly, alkylaminoalkyl and dialkylaminoalkyl refer to lower alkyl groups and lower alkylene chains connected by a secondary (—NH—) or tertiary (N≡) amino group. $R^7$ is selected from hydrogen, lower alkyl, phenyl-loweralkylene, or phenylthio-lower-alkylene. The letter n denotes the integer 2 or 3. X may be a chemical bond, an oxygen or sulfur atom, a sulfoxide group

or —$NR^9$—, wherein $R^9$ is hydrogen, lower alkyl, phenyl, or phenyl-lower-alkylene. There is the proviso that when X is a chemical bond, Z can only be a 3-indolyl moiety. Z is selected from the group comprising phenyl substituted with 1 to 3 substituents independently selected from among hydrogen, lower alkyl, or lower alkoxy, phenyl-loweralkylene, or 3-indolyl.

Preferred compounds of the instant invention have the structure of Formula I wherein $R^2$, $R^5$, $R^6$, and $R^7$ are lower alkyl, X is a sulfur atom or $NR^9$ and Z is phenyl. In the most preferred compounds, n is 2, $R^7$ is methyl, and X is either a sulfur atom or $NR^9$.

The compounds of the present invention can exist as optical isomers and both the racemic mixtures of these isomers as well as the individual optical isomers themselves are within the scope of the present invention. The racemic mixtures can be separated into their individual isomers through well known techniques such as the separation of the diesteriomeric salts formed with optically active acids, followed by conversion back to the optically active bases.

As indicated, the present invention also pertains to the pharmaceutically acceptable non-toxic salts of these basic compounds. Such salts include those derived from organic and inorganic acids such as, without limitation, hydrochloric acid, hydrobromic acid, phosphoric acid, sulfuric acid, methanesulfonic acid, acetic acid, tartaric acid, lactic acid, succinic acid, citric acid, maleic acid, sorbic acid, aconitic acid, salicylic acid, phthalic acid, embonic acid, enanthic acid, and the like.

The compounds of the present invention may be produced by the following processes which employ variations of the Hantzsch synthetic reaction applied to the appropriate starting materials.

Specifically, the present invention utilizes a modified Hantzsch process for preparation of the compounds of Formula I according to the reaction schemes followed hereinbelow. The general reaction process and many of the required intermediate compounds have been previously described in U.S. Pat. No. 4,414,213 which is hereby incorporated herein by reference.

General processes for the preparation of compounds of Formula I may be viewed as variations of the unitary process shown in Scheme 1.

Scheme 1
General Synthesis

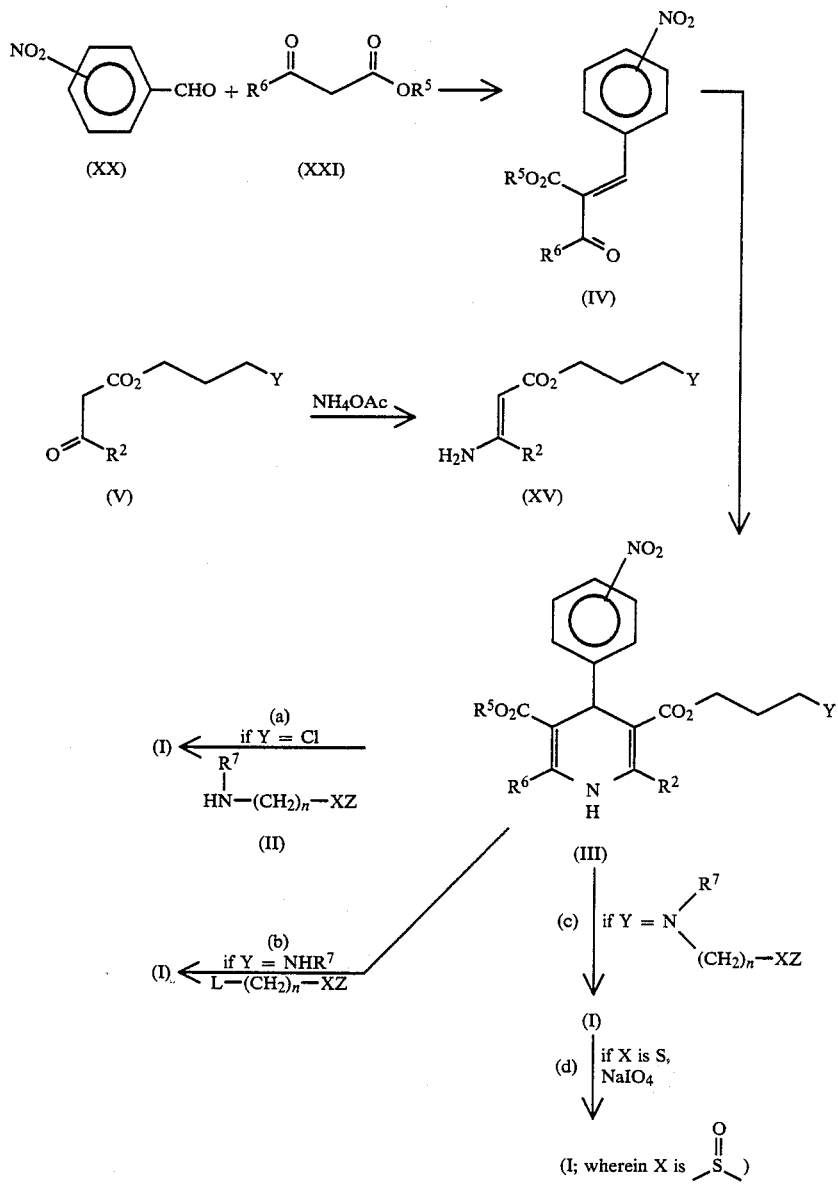

In the foregoing general synthesis outlined in Scheme 1, $R^2$, $R^5$, $R^6$, $R^7$, $R^9$, n, X, and Z are as defined for Formula I. Y may be either a halogen such as chloride; $NHR^9$; or $N(R^7)(CH_2)_nXZ$. L denotes a leaving group as understood in organic synthesis: examples being a halide, e.g. bromide, a mesylate or tosylate or the like.

Preparation of the compounds of Formula I according to the process of the general synthesis comprises preparation of Formula III compounds by heating IV-type and XV-type intermediate compounds either neat or in the presence of a wide variety of reaction inert organic solvents. Suitable solvents include but are not limited to benzene, toluene, tetrahydrofuran, dibutylether, butanol, hexanol, methanol, dimethoxyethane, ethylene glycol, ethanol, propanol, etc. Suitable reaction temperatures are from about 60°–150° C. No other catalyst or condensation agent is usually required. The requisite intermediate enamine esters (XV) are generated under aminolysis reaction conditions ($NH_4OAc$/alcohol) from V intermediates. The XV intermediates are usually not isolated but are allowed to react immediately with the appropriate IV intermediate compounds. The intermediate acylcinnamate compounds of structure IV are prepared in general by utilizing known Knoevenagel condensation reaction conditions. In general, appropriate nitrobenzaldehydes (XX) and 1,3-dicarbonyl compounds (XXI) are condensed to give IV.

The Formula III compounds are then converted to the appropriate Formula I product by selecting a process step according to the structure of substructure Y. If Y is $N(R^7)(CH_2)_nXZ$, then III=I, as shown in (c). If Y is Cl, then III is reacted with a compound II intermediate to give I, as shown in (a). If Y is NHR[7], then III is reacted with a compound XII intermediate to give I, as shown in (b). Finally, if X of I is sulfur, then I may be oxidized with sodium periodate in alcohol to give the sulfoxide product, as shown in (d).

These variations of the general synthesis are shown in somewhat greater detail in the reaction schemes which follow.

Scheme 2

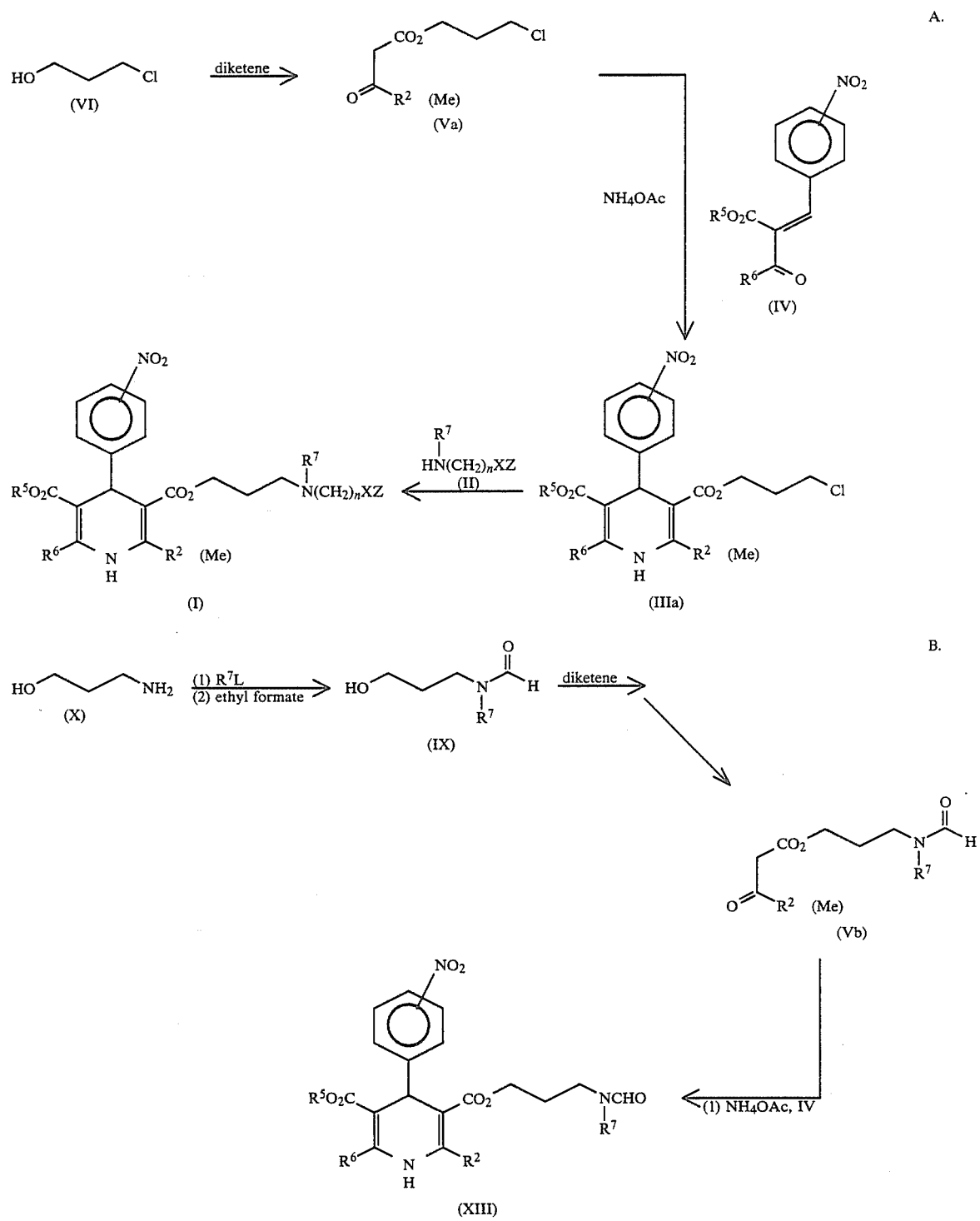

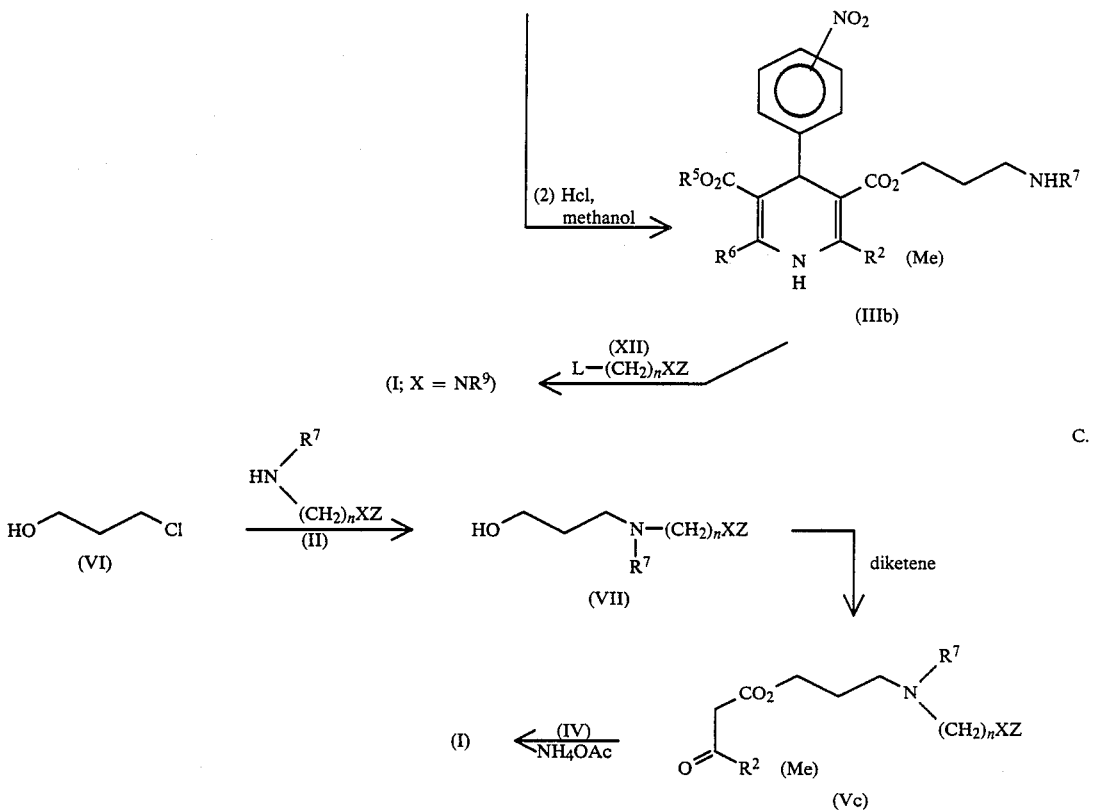

As shown in Scheme 2, an intermediate 1,3-dicarbonyl compound (Va-c), generated by treatment of either a chloroalkanol (VI), a formamide (IX) or the aminoalkanol (VII) with either diketene or with Meldrum's acid; is subjected to modified Hantzsch condensation conditions (ammonium acetate/ethanol) followed by reaction with the cinnamate intermediate (IV) as in A and C or, following hydrolysis of XIII to give IIIb, with intermediate XII as in B to afford a desired product of Formula I. While the syntheses shown in Scheme 2 exemplify the use of diketene, and hence define R² as methyl, Meldrum's acid may be used as shown in Scheme 3. Meldrum's acid is described in the Merck Index, 10th Edition, 5635, page 828 (1983).

Scheme 3

Compounds Where R² is to be Other Than Methyl

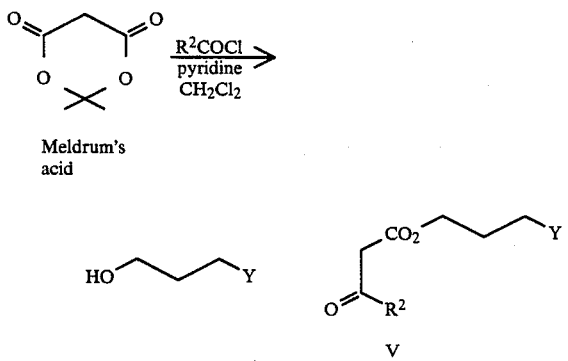

For more details of the use of Meldrum's acid as a $C_3O_2$ synthon, cf: Y. Oikawa, et al., *J. Org. Chem.* 43, 2087 (1978).

The compounds of this invention have been found to possess several useful pharmacologic properties, including calcium ion blocker activity, inhibition of ischemia-induced tissue injury and inhibition of blood platelet aggregation. These pharmacologic properties are considered to be predictive of usefulness in treating cardiovascular disease with compounds of the instant invention. Specifically, compounds which possess anti-ischemia activity and/or platelet anti-aggregtion properties, in addition to calcium blocking action, possess a unique biological profile suggesting application in the treatment of myocardial ischemia, hypertension, intermittant claudication, and/or congestive heart failure.

Calcium ion entry blockade was studied in various smooth muscle systems such as rat dorsal aorta, portal vein, and trachea. In general, preferred compounds of the instant invention possess calcium entry blockade activities similar or with improved potency compared with the reference compound Nicardipine.

Selected compounds of the instant invention were also examined in in vitro and in vivo laboratory tests developed to demonstrate a drug's potential for protecting cardiac tissue from injury due to ischemia (cf: Rosenberger, et al., *Life Sci.*, 34, 1379 (1984)). These tests utilize the known relationship between progressive depletion of high energy phosphate and the onset of lethal cell injury in ischemic myocardium. Results of these screening tests demonstrate that the selected compounds possess potent anti-ischemia action. This activity distinguishes the compounds of the instant invention from the reference compound Nicardipine which fails to provide any protection against autolysis caused by ischemia.

Finally, compounds of the instant invention exhibit potent inhibition of various aspects of blood platelet function. Representative of these effects is the ability of the instant compounds to inhibit collagen-induced aggregation of blood platelets.

In summary, considering the biological activity indicated by the pharmacological testing described hereinabove, the instant compounds have cardiovascular properties particularly suited to their use in hypertension and ischemia-related disorders. Thus, another aspect of the instant invention concerns a process for ameliorating either hypertension or an ischemia-related disorder in a mammal in need of such treatment which comprises systemic administration to such mammal of an effective dose of a Formula I compound or a pharmaceutically acceptable acid addition salt thereof.

Generally, the compounds of the instant invention will be administered in the same manner as for the reference drug Nifedipine and the daily oral dose will comprise from about 10 to about 60 mg, preferably 10–20 mg administered from 1 to 3 times a day. In some instances, a sufficient therapeutic effect can be obtained at lower doses while in others, larger doses will be required. It is understood that for clinical application, the dosage and dosage regimen must in each case be carefully adjusted, utilizing sound professional judgment and considering the age, weight and condition of the recipient, the route of administration and the nature and gravity of the illness. Administration of the compounds of the instant invention by the oral route is preferred.

The term "systemic administration" as used hereinabove refers to oral, rectal, and parenteral (i.e. intramuscular, intravenous, and subcutaneous) routes. Generally, it will be found that when a compound of the present invention is administered orally, which is the preferred route, a larger quantity of reactive agent is required to produce the same effect as a smaller quantity given parenterally. In accordance with good clinical practice, it is preferred to administer the instant compounds at a concentration level that will produce effective anti-hypertensive and/or anti-ischemic effects without causing any harmful or untoward side effects.

Therapeutically, the instant compounds are generally given as pharmaceutical compositions comprised of an effective antihypertensive and/or anti-ischemic amount of a compound of Formula I or a pharmaceutically acid addition salt thereof and a pharmaceutically acceptable carrier. Pharmaceutical compositions for effecting such treatment will contain a major or minor amount, e.g. from 95 to 0.5% of at least one compound of the present invention in combination with a pharmaceutical carrier, the carrier comprising one or more solid, semi-solid, or liquid diluent, filler, and formulation adjuvant which is non-toxic, inert and pharmaceutically acceptable. Such pharmaceutical compositions are preferably in dosage unit forms; i.e. physically discrete units containing a pre-determined amount of the drug corresponding to a fraction or multiple of the dose which is calculated to produce the desired therapeutic response. The dosage units can contain one, two, three, or more single doses, or, alternatively, one-half, one-third, or less of a single dose. A single dose preferably contains an amount sufficient to produce the desired therapeutic effect upon administration at one application of one or more dosage units according to the pre-determined dosage regimen usually a whole, half, third or quarter of the daily dosage administered once, twice, three or four times a day. Other therapeutic agents can also be present. Pharmaceutical compositions which provide from about 1 to 50 mg of the active ingredient per unit dose are preferred and are conventionally prepared as tablets, lozenges, capsules, powders, aqueous or oily suspensions, syrups, elixirs, and aqueous solutions. Preferred oral compositions are in the form of tablets or capsules and may contain conventional excipients such as binding agents (e.g. syrup, acacia, gelatin, sorbitol, tragacanth, or polyvinylpyrrolidone), fillers (e.g. lactose, sugar, maizestarch, calcium phosphate, sorbitol, or glycine), lubricants (e.g. magnesium stearate, talc, polyethylene glycol or silica), disintegrants (e.g. starch) and wetting agents (e.g. sodium lauryl sulfate). Solutions or suspensions of Formula I compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propylene glycol, and polyethylene glycols or mixtures thereof. The polyethylene glycols consist of a mixture of non-volatile, usually liquid, polyethylene glycols which are soluble in both water and organic liquids and which have molecular weights from about 200 to 1500.

DESCRIPTION OF THE SPECIFIC EMBODIMENTS

The compounds which constitute this invention and their methods of preparation will appear more fully from a consideration of the following examples which are given for the purpose of illustration only and are not to be construed as limiting the invention in sphere or scope. All temperatures are understood to be in degrees Centigrade when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), singlet (s), multiplet (m), doublet (d), doublet of doublets (dd), triplet (t), or quartet (q). Abbreviations employed are DMSO-$d_6$ (per-deuterodimethylsulfoxide), $CDCl_3$ (deuterochloroform) and are otherwise conventional. The infrared (IR) spectral descriptions include only absorption vg wave numbers ($cm^{-1}$) having functional group identification value. The IR determinations were employed using potassium bromide (KBr) as diluent. All compounds gave satisfactory elemental analyses.

Synthesis of Intermediates

A. Intermediates of Formula IV

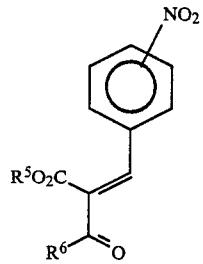

IV

EXAMPLE 1

Methyl 2-[(3-Nitrophenyl)methylene]-3-oxobutanoate

A solution of 151 g (1.00 mole) of 3-nitrobenzaldehyde, 116 g (1.00 mole) of methyl acetoacetate, 10 mL of glacial acetic acid, 4 mL of piperidine, and 400 mL of benzene was refluxed 2 hr during which time 21 mL of water was removed via a Dean-Stark trap. The dark yellow solution was cooled to ambient temperature and solidification occurred. Filtration followed by washing with ether afforded 180 g of product as a yellow solid. An additional 23 g product was obtained from the filtrate to yield a total of 203 g (82%) of product, m.p. 145°–146° C. (literature m.p. 158° C.; cf: Meyer, et al., *Arzneim.-Forsch/Drug Research*, 31, 407 (1981).

EXAMPLE 2

Ethyl 2-[(3-Nitrophenyl)methylene]-3-oxobutanoate

This compound was prepared in molar scale according to the method described above in Example 1 and substituting ethyl acetoacetate for the methyl ester. Recrystallization from ethanol yielded 182 g (69%) of product as a yellow solid, m.p. 103°–106° C. (literature m.p. 110° C.; cf: Ruhemann, *J. Chem. Soc.*, 83, 717 (1903).

Additional examples of intermediates of Formula IV which were prepared using the procedures given above are listed in Table 1.

TABLE 1
Formula IV Intermediate Compounds

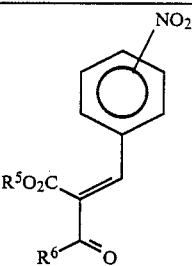

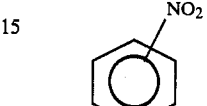

| Ex | | $R^5$ | bp (°C./0.1 mm) | mp (°C.) |
| --- | --- | --- | --- | --- |
| 3 | 4-nitro | ethyl | — | 59.5–61.5 |
| 4 | 3-nitro | 2-chloroethyl | — | 68–76 |
| 5 | 3-nitro | 3-chloropropyl | — | — |
| 6 | 2-nitro | methyl | — | oil |
| 7 | 3-nitro | methoxyethyl | — | — |
| 8 | 4-nitro | dimethylaminoethyl | — | — |

B. Intermediates of Formula V

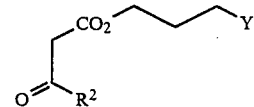

V

EXAMPLE 9

3-Chloropropyl Acetoacetate (Va)

3-Chloropropanol (47.3 g, 0.50 mole) and a catalytic amount of triethylamine at 65° were treated dropwise with 42 g (0.50 mole) of diketene. After the addition was complete, the reaction was stirred at 65° for an additional hour. Distillation of the residue furnished 72.9 g (82%) of product as a clear liquid, b.p. 78°–85° at 150 mm.

EXAMPLE 10

[3-(Butylformamido)propyl] Methyl Acetoacetate (Vb)

A solution of 3-aminopropanol (X, 37.6 g, 0.50 mole) in 200 mL of dry acetonitrile was treated with n-butyl bromide (69.6 g, 0.56 mole) and then refluxed for 16 hour. The solution was concentrated in vacuo and 150 mL of water added and the mixture was then made basic with sodium hydroxide. Extraction with methylene chloride and concentration of the extracts yielded 47.2 g of crude hydroxypropyl secondary amine which was taken up in 100 mL of ethyl formate, allowed to stand overnight at room temperature, and then the volatile substances were removed in vacuo. Kugelrohr distillation of the residue (bp 126° C./1.2 mm) afforded 26.9 g (34% yield from X) of formamide intermediate (IX) as a clear liquid.

The formamide was treated with 0.5 mL of triethylamine and then diketene (14.2 g, 0.17 mole) was slowly added to the stirred reaction liquid. The reaction was kept cool by use of an ice bath during the diketene reaction. After 10 minutes, the addition was complete and the orange liquid was allowed to stir an additional 30 minutes at room temperature to give Vb which was used without further purification.

EXAMPLE 11

3-[[2-[(N-Methyl-N-phenyl)amino]ethyl]-N'-(phenylmethyl)amino]propyl] Methyl Acetoacetate (Vc)

These intermediate Vc compounds were usually generated in situ just prior to their conversion to product I compounds.

A mixture of N-methyl-N-phenyl-N'-phenylmethylethylenediamine (II, 10.3 g, 42.9 mmole); 3-chloropopanol (4.73 g, 50.0 mmole); micropulverized potassium carbonate (5.9 g, 43 mmole); and a catalytic amount of sodium iodide (approximately 25 mg) was taken up in 75 mL of acetonitrile and refluxed for 6 days. The mixture was concentrated in vacuo and the residue taken up in methylene chloride and washed successively with water, 10% aqueous HCl (vol:vol), water, 10% aqueous NaOH (wt:vol), water, and brine. After drying over potassium carbonate, the solvent was removed in vacuo to yield 13.3 g of a light yellow oil. This material was flash chromatographed (silica:5% methanol/chloroform) and furnished 5.5 g (41%) of a VII intermediate compound as a colorless oil. A small portion of the intermediate oil was converted to the oxylate salt (m.p. 100°-102°).

The Vc product was generated in situ by adding an equivalent amount of diketene in a dropwise fashion to the VII product oil (no solvent used) in an oil bath heated to 100°.

EXAMPLE 12

3-[N-(Phenylmethyl)-N'-[2-(phenylthio)ethyl]amino]propyl Methyl Acetoacetate (Vc)

This intermediate product was generated in situ using similar methodology to that described above in Example 11 but beginning with N-phenylmethyl-N'-phenylthio-ethylenediamine (II) as the starting diamine. The intermediate VII compound (bp 170°/0.1 mm) was obtained in 58% yield following Kugelrohr distillation of the crude reaction oil. The appropriate Vc product was generated in situ by treatment of the intermediate oil with diketene.

C. Intermediates of Example III

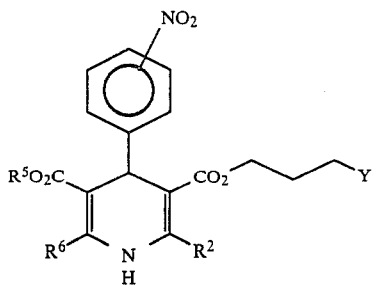

EXAMPLE 13

(3-Chloropropyl) Methyl 1,4-Dihydro-2,6-dimethyl-4-(3-nitrophenyl)-3,5-pyridinedicarboxylate (IIIa)

Ammonium acetate (3.85 g, 50.0 mmole) was added to a solution of 3-chloropropyl acetoacetate (Example 9, 8.15 g, 50.0 mmole) and 50 mL of absolute ethanol, and then refluxed under nitrogen for one hour. Methyl 2-[(3-nitrophenyl)methylene]-3-oxobutanoate, prepared (cf: Example 1) by the condensation of 3-nitrobenzaldehyde with methyl acetoacetate; (12.5 g, 50.0 mmole) was then added and the resulting yellow solution refluxed an additional 12 hr. After cooling to room temperature, the solvent was removed in vacuo and the residue recrystallized from ethanol to yield the desired IIIa product as yellow solid, m.p. 125°-130°.

NMR (DMSO-$d_6$): 2.04 (2,m); 2.35 (6,s); 3.42 (2,t, 6.5 Hz); 3.64 (3,s); 4.20 (2,q,6.3 Hz); 5.07 (1,s); 7.40 (2,m); 7.64 (1,m); 8.05 (2,m).

IR (KBr): 705, 1100, 1120, 1215, 1350, 1490, 1530, 1650, 1685, 1700, 3370.

EXAMPLE 14

[3-(Butylamino)propyl] Methyl 1,4-Dihydro-2,6-dimethyl-4-(3-nitrophenyl)-3,5-pyridinedicarboxylate (IIIb)

To a solution of n-butylformamidopropyl acetoacetate (Vb, 23.1 g, 0.10 mole) in 250 mL of absolute ethanol was added ammonium acetate (7.7 g, 0.10 mole) and the resulting solution was refluxed under nitrogen 2 hour. Methyl 2-[(3-nitrophenyl)methylene]-3-oxobutanoate (IV, 24.9 g, 0.10 mole) was added and the yellow solution was then refluxed 17 hour. The reaction was concentrated in vacuo to yield 57 g of crude XIII as a dark yellow liquid. This residual liquid was taken up in 500 mL of absolute methanol to which concentrated hydrochloric acid (8.3 mL, 0.10 mole) was added, and the resulting solution refluxed under nitrogen. After 24 hours, the solution was cooled to ambient temperature and concentrated in vacuo. The resulting material was taken up in methylene chloride and these extracts were washed with aqueous ammonium hydroxide, water, and then brine. The combined methylene chloride extracts were then dried (MgSO$_4$), filtered, and the filtrate concentrated in vacuo to yield 45.8 g of a dark yellow oil. Purification by flash chromatography (silica 5% methanol/chloroform) furnished 16.9 g (38%) of product IIIb as a yellow oil. For characterization, a small portion of the oil was converted to the tosylate salt and recrystallized from acetonitrile to yield yellow solid, m.p. 142°–146°.

Intermediates of Formula II

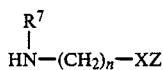

Many of the amino compounds of Formula II are commercially available and most others may be prepared by following published procedures which may be readily found in the literature by one skilled in the art of organic synthesis; see, e.g. U.S. Pat. No. 4,381,401. Many of the requisite intermediate compounds of Formula II may be prepared according to a general procedure exemplified by the following syntheses.

EXAMPLE 15

General Procedure for the Preparation of Compounds of Formula II

Following previously published accounts, such as U.S. Pat. No. 4,381,401, equimolar quantities (50–100 mmole) of an appropriate oxazolidinone (see, e.g. Examples 17, 18), aniline hydrochloride and/or thiophenol, and a catalytic amount of lithium chloride (added to the reaction mixture to increase the rate of reaction and to minimize side products) were stirred under a nitrogen atmosphere and heated with an oil bath which was kept in a temperature range of 150°–170°. After reaching oil bath temperatures, dissolution occurred and gas evolution began. After 5–24 hour (as determined by cessation of gas evolution or by TLC assay of the crude reaction mixture) the contents were allowed to cool to room temperature. Product compounds wherein X is nitrogen (diamine hydrochloride compounds) were purified by recrystallization from ethanol/ether mixtures. Amino ethyl sulfides (X=sulfur) were converted to their hydrochloride salts by treatment with 6.5N ethanolic HCl and then recrystallized from ethyl ether mixtures.

EXAMPLE 16

N-Methyl-3-(phenylthio)propanamine Hydrochloride

This compound is prepared using a similar procedure to Example 15 but employing an oxazinone instead of an oxazolidinone as in Example 15.

Thiophenol (2.75 g, 25.0 mmole), tetrahydro-3-methyl-2H-1,3-oxazin-2-one (Example 19, 2.88 g, 25.0 mmole) and a catalytic amount (about 5 mg) of lithium chloride were heated under nitrogen in an oil bath held at 170°. After 5 hours, the yellow solution was cooled to room temperature and purified by Kugelrohr distillation (bp 85°/0.3 mm) to furnish 3.4 g (72%) of product as a clear liquid. A small sample of the base was converted to the hydrochloride salt and recrystallized from ethanol/ether to yield a colorless white solid, m.p. 119°–121°.

EXAMPLE 17

3-(Phenylmethyl)-2-oxazolidinone ($R^7=CH_2Ph$) (Intermediate for Preparation of Formula II Compounds)

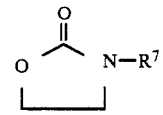

A cold (ice-bath) suspension of sodium hydride (0.55 mole, hexane washed) in 100 mL of dry THF was stirred under a nitrogen atmosphere while a solution of 2-oxazolidinone in 500 mL of 10:1 THF:DMF was added dropwise. The resulting gray suspension was warmed to room temperature and stirred for 24 hour. Benzyl bromide (66 mL, 0.056 mole) was added to the resulting white suspension and stirred at ambient temperature 24 hour. The reaction was quenched by careful addition of 26 mL water and the resulting mixture was concentrated and poured into 500 mL of water. After extraction with methylene chloride, the combined extracts were washed with water and brine and dried over magnesium sulfate. Concentration in vacuo afforded 104 g of a yellow oil which was purified by Kugelrohr distillation (bp 100°/0.1 mm) to give 81 g (92% yield) of the product as a colorless liquid which solidified on standing at room temperature to a colorless solid, m.p. 76°–78°.

EXAMPLE 18

3-[2-(Phenylthio)ethyl]-2-oxazolidinone ($R^7=CH_2CH_2SPh$)

Following a procedure similar to that used in Example 17 except that bromoethyl phenyl sulfide was substituted for benzyl bromide, the product oxazolidinone was isolated in 17% as a yellow oil after chromatography (silica:CHCl₃).

EXAMPLE 19

Tetrahydro-3-methyl-2H-1,3-oxazin-2-one ($R^7=CH_3$)

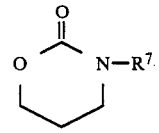

A suspension of hexane-washed sodium hydride (0.10 mole, in 50 mL dry THF) was stirred under a nitrogen atmosphere while a solution of tetrahydro-2H-1,3-oxazin-2-one (8.20 g, 0.0812 mole) in 50 mL THF was slowly added. After stirring the resulting suspension 5 hour at room temperature, methyl iodide (28 g, 0.02 mole) was added and the mixture stirred overnight. Water (5 mL) was added to quench the reaction and the solution was poured into 500 mL brine. After continuously extracting the solution with methylene chloride for 6 days, the organic portion was concentrated to yield 7.8 g of crude product. Purification by Kugelrhor distillation (bp 101°/0.4 mm) afforded 6.7 g (72% yield) of product as a clear liquid.

Additional examples of intermediates of Formula II which were prepared using adaptations of intermediates and procedures given above are listed in Table 2.

TABLE 2

Formula II Intermediate Compounds $$\underset{HN-(CH_2)_n XZ}{\overset{R^7}{|}} \quad II$$

| Ex. | R[7] | n | XZ | mp (°C.) of HCl Salt |
|---|---|---|---|---|
| 20 | Me | 2 | NHPh | 160–162 |
| 21 | Me | 2 | N(Me)Ph | 149–150 |
| 22 | CH₂Ph | 2 | N(Me)Ph | 169–170 |
| 23 | Me | 2 | N(Me)Ph | 157–159 |
| 24 | H | 2 | SPh | 107–125 |
| 25 | Me | 2 | SPh | 95–96 |
| 26 | CH₂Ph | 2 | SPh | 154–155 |
| 27 | Me | 2 | 2-MeOPh | 101–103 |
| 28 | Me | 2 | S(4-t-Bu—2-MePh) | —(a) |
| 29 | CH₂CH₂SPh | 2 | SPh | 90–100 |

(a)Isolated as free base via Kugelrohr distillation, bp 110°/0.9 mm.

Synthesis of Products

The following is the general procedure for the preparation of the products of Formula I using synthetic pathway (a) of Scheme 1.

EXAMPLE 30

General Procedure for Synthesis (a) of Compounds of Formula I

A solution of chloropropyl dihydropyridine (IIIa, 4.09 g, 10.0 mmole) a Formula II intermediate amino compound (20–30 mmole), triethylamine (2.1 g, 20 mmole), and sodium iodide (10–20 mg), in 35–50 mL of acetonitrile was refluxed under nitrogen for several days or until TLC analysis indicated the disappearance of IIIa. The solution was concentrated in vacuo and the residue taken up in methylene chloride and washed with water, 10% aqueous HCl (vol:vol), water, 5% aqueous NaOH (wt:vol), water, and then brine. The solution was dried over potassium carbonate, filtered, and concentrated in vacuo to afford crude I as a yellow oil. The oily products were purified by flash chromatography (silica:methanol/chloroform eluants) and then converted to their hydrochloride salts. In most instances, these products were amorphous yellow solid which did not display sharp melting points. The compounds did give satisfactory analytical data (±0.4% for C, H, N, see Table 4 hereinbelow), and displayed spectral characteristics (IR, MS, proton-NMR) which were consistent with their assigned structures.

EXAMPLE 31

Methyl [3-[N-Methyl-N-[2-(phenylthio)ethyl]amino]propyl] 1,4-Dihydro-2,6-dimethyl-4-(3-nitrophenyl)-3,5-pyridinedicarboxylate Hydrochloride A solution of dihydropyridine IIIA (Ex. 13, 4.08 g, 10.0 mmole), amino sulfide II (Ex. 25, 3.10 g, 20.0 mmole), triethylamine (2.1 g, 20 mmole), and a catalytic amount of sodium iodide was refluxed 3 days in 50 mL of dry acetonitrile. The mixture was concentrated in vacuo and the residue taken up in 100 mL of methylene chloride. After washing with 5% aqueous HCl solution, water, 5% aqueous NaOH solution, water and brine, the organic phase was dried over anhydrous potassium carbonate and filtered. Removal of the volatiles in vacuo afforded 5.4 g of crude product as a yellow oil. Purification by flash chromatography (silica:CHCl₃; and then 1%, 2.5%, and 5% methanol/CHCl₃ as eluant) furnished 2.9 g (54% yield) of product as a yellow oil. Conversion to the hydrochloride salt was effected by treatment with 6.5N ethanolic hydrogen chloride. The product was recrystallized from ethanol and collected as a yellow solid, m.p. 137°–140° C.

Representative examples of I products prepared in this manner are shown in Table 3.

TABLE 3

Formula I Products

| Ex. | R[7] | N | XZ | Hydrochloride Salt mp (°C.) |
|---|---|---|---|---|
| 32 | H | 2 | NHPh | i (indistinct) |
| 33 | H | 2 | 3-indolyl | i |
| 34 | Me | 2 | SPh | 137–140 |
| 35 | H | 2 | OPh | i |
| 36 | Me | 2 | N(Me)Ph | 96–105 |
| 37 | Me | 2 | NHPh | 109–115 |
| 38 | Me | 2 | N(CH₂Ph)Ph | i |
| 39 | Me | 2 | S(4-t-Bu—2-MePh) | i |
| 40 | Me | 3 | SPh | i |
| 41 | Me | 2 | S(2-MeOPh) | i |
| 42 | H | 2 | SPh | 91–95 |
| 43 | CH₂CH₂SPh | 2 | SPh | i |

The following example is illustrative of the general procedure for the preparation of products of Formula I using synthetic pathway (b) of Scheme 1.

EXAMPLE 44

[3-[[N-Butyl-N-(2-phenoxyethyl)]amino]propyl]Methyl 1,4-Dihydro-2,6-dimethyl-4-(3-nitrophenyl)-3,5-pyridinedicarboxylate Hydrochloride Hemihydrate A solution comprising [3-(butylamino)propyl]methyl 1,4-dihydro-2,6-dimethyl-4-(3-nitrophenyl)-3,5-pyridinedicarboxylate (IIIb, 4.26 g, 9.57 mmole); β-bromophenotole (2.01 g, 10 mmole); 10 mmole of triethylamine; and 50 mL of acetonitrile was refluxed under nitrogen for 24 hour. The mixture was concentrated in vacuo, taken up in methylene chloride, and then washed with water and brine. After drying over potassium carbonate, the methylene chloride solution was filtered and the filtrate was concentrated in vacuo to yield 6.1 g of crude product as a dark yellow liquid. Purification was effected by flash chromatography (silica: 1% methanol/chloroform) to afford 3.0 g (57%) of the base form of the product as a yellow oil. Treatment of the base with 6.5N ethanolic HCl effected conversion to the hydrochloride salt which was isolated as a yellow foam (melting point indistinct).

The following examples are illustrative of the general procedure for the preparation of products of Formula I using synthetic pathway (c) of Scheme 1.

EXAMPLE 45

[3-[[[2-(N-Methyl-N-phenyl)amino]ethyl]-N'-phenylmethyl]propyl]Methyl 1,4-Dihydro-2,6-dimethyl-4-(3-nitrophenyl)-3,5-pyridinedicarboxylate Dihydrochloride Sesquihydrate As described in Example 11, 3-[[2-[(N-methyl-N-phenyl)amino]ethyl]-N'-phenylmethyl)amino]propyl] methyl acetoacetate (Vc) was generated in situ by adding diketene (1.25 g, 15.0 mmole) dropwise to 4.47 g, (15.0 mmole) of the VII intermediate while being heated in a 100° oil bath. After the addition was complete, 50 mL of ethanol and ammonium acetate (1.15 g, 14.9 mmole) were added and the resulting solution was refluxed 4 hour. Methyl 2-[(3-nitrophenyl)methylene]-3-oxobutanoate (IV, 3.7 g, 14.9 mmole) was added and the resulting solution refluxed for an additional 18 hour. The reaction mixture was concentrated in vacuo and the residue purified by flash chromatography (silica:methanol/chloroform solutions) to furnish 2.3 g (25%) of I product as a yellow oil. This material was converted to the dihydrochloride salt by treatment with ethanolic HCl and isolated as a yellow foam, m.p. 75°–85°.

$^1$HNMR (DMSO-d$_6$): δ 2.36 (s,6), 2.28 (m,2), 2.91 (s,3), 3.20 (m,4), 3.60 (s,3), 4.00 (m,4), 4.42 (s,2), 5.00 (s,1), 6.78 (m,2), 7.20 (m,2), 7.50 (m,8), 8.02 (m,2), 9.30 (bs,1), and 11.60 (bs,1).

IR (KBr): 3100, 2600, 1695, 1530, 1490, 1350, 1215, 1120, 1100, 750, and 750 cm$^{-1}$.

EXAMPLE 46

Methyl [3-[N-(Phenylmethyl)-N-[2-(phenylthio)ethyl]amino]propyl] 1,4-Dihydro-2,6-dimethyl-4-(3-nitrophenyl)-3,5-pyridinedicarboxylate Hydrochloride Starting with 3-[N-(phenylmethyl)-N'-[2-(phenylthio)ethyl]amino]propyl] methyl acetoacetate (Vc) generated in situ, the corresponding I product was prepared in 60% yield using methodology similar to that described above in Example 45. The product was isolated in the form of a yellow, amorphous hydrochloride salt which displayed an indistinct melting point.

The following example is illustrative of the general procedure for the preparation of products of Formula I using synthetic pathway (d) of Scheme 1.

EXAMPLE 47

Methyl [3-[N-Methyl-N-[2-phenylsulfinyl)ethyl]amino]propyl] 1,4-Dihydro-2,6-dimethyl-4-(3-nitrophenyl)-3,5-pyridinedicarboxylate Hydrochloride Hydrate Following the general oxidative method of Leonard and Johnson, *J. Org. Chem.* (1961), 27, page 282; a solution of methyl [3-[N-methyl-N-[2-(phenylthio)ethyl]amino]propyl]1,4-dihydro-2,6-dimethyl-4-(3-nitrophenyl)-3,5-pyridinedicarboxylate (Example 34; 2.32g, 3.99 mmole) in 50 mL of methanol was treated with sodium periodate (0.96 g, 4.4 mmole) dissolved in 50 mL of water. The resulting solution was stirred at room temperature overnight (18 hour) and water was added. After extraction with methylene chloride, the combined organic portions were dried over sodium sulfate, filtered, and concentrated in vacuo to yield 1.8 g of a yellow foam. Flash chromatography (silica:methanol/chloroform) furnished 1.24 g (50%) of I product wherein X is sulfoxide as a yellow oil. The free base oil was converted to the hydrochloride salt and isolated as a yellow foam, m.p. 80°–95°.

As mentioned hereinabove, most Formula I products were generally thick oils which could be converted to amorphous yellow solids when converted to the hydrochloride salt. In most instances, these hydrochloride salts did not display sharp melting points but they did given satisfactory analytical data and examples of these are shown below in Table 4.

TABLE 4
Elemental Analyses of HCl Salts of Formula I Compounds

| Ex. No. | Empirical Formula | Calcd C | Calcd H | Calcd N | Found C | Found H | Found N |
|---|---|---|---|---|---|---|---|
| 32 | $C_{27}H_{32}N_4O_6$ 1.3HCl | 58.33 | 6.04 | 10.08 | 58.16 | 6.17 | 9.93 |
| 33 | $C_{29}H_{32}N_4O_6$ 1.4HCl | 59.68 | 5.77 | 9.60 | 59.90 | 5.85 | 9.34 |
| 34 | $C_{28}H_{33}N_3O_6S$ HCl | 58.38 | 5.95 | 7.29 | 58.12 | 6.11 | 7.32 |
| 35 | $C_{27}H_{31}N_3O_7$ HCl | 59.39 | 5.91 | 7.70 | 59.19 | 5.94 | 7.71 |
| 36 | $C_{29}H_{36}N_4O_6$ 1.1HCl | 60.40 | 6.48 | 9.71 | 60.16 | 6.54 | 9.59 |
| 37 | $C_{28}H_{34}N_4O_6$ HCl 0.5 H$_2$O | 59.20 | 6.03 | 9.86 | 58.89 | 6.37 | 9.62 |
| 38 | $C_{35}H_{40}N_4O_6$ HCl 0.4 H$_2$O | 64.04 | 6.42 | 8.54 | 63.91 | 6.46 | 8.48 |
| 39 | $C_{33}H_{43}N_3O_6S$ HCl | 61.33 | 6.86 | 6.50 | 61.18 | 6.93 | 6.24 |
| 40 | $C_{29}H_{35}N_3O_6S$ HCl | 59.02 | 6.15 | 7.12 | 58.68 | 6.15 | 6.97 |
| 41 | $C_{29}H_{35}N_3O_7S$ HCl | 57.47 | 5.99 | 6.93 | 57.23 | 6.03 | 6.77 |
| 42 | $C_{27}H_{31}N_3O_6S$ HCl 0.3 H$_3$O | 57.14 | 5.79 | 7.41 | 57.02 | 5.82 | 7.46 |
| 43 | $C_{35}H_{39}N_3O_6S_2$ HCl | 60.20 | 5.78 | 6.02 | 60.07 | 5.82 | 6.30 |
| 44 | $C_{31}H_{39}N_3O_7$ HCl 0.5 H$_2$O | 60.93 | 6.76 | 6.88 | 60.98 | 6.80 | 6.73 |
| 45 | $C_{35}H_{40}N_4O_6$ 2HCl 1.5 H$_2$O | 58.99 | 6.36 | 7.86 | 58.70 | 5.96 | 7.54 |
| 46 | $C_{34}H_{37}N_3O_6S$ HCl | 62.61 | 5.87 | 6.44 | 62.43 | 5.90 | 6.45 |
| 47 | $C_{28}H_{33}N_3O_7S$ HCl 0.25 H$_2$O | 56.37 | 5.83 | 7.04 | 56.17 | 6.16 | 6.90 |

Biological Activities of Formula I Compounds

The more relevant biological activities for the compounds of Formula I of the instant series are calcium block, anti-ischemic activity, and inhibition of platelet aggregation. The biological test data reflecting these activities is displayed in Table 5 for selected examples of compounds of the instant series.

TABLE 5
Biological Test Data for Selected Formula I Compounds

| Ex. No. | Calcium Entry Blockade(pA$_2$)[a] | Autolysis (% Protection)[b] | Aggregometry (EC$_{50}$ mg/mL)[c] |
|---|---|---|---|
| Nifedipine | 9.48 | 21 | 176 |
| Nicardipine | 8.95 | 0 | —[d] |
| 32 | 8.53 | 0 | 25 |
| 33 | 10.5 | 35 | 20 |
| 34 | 9.90 | 43 | 12.6 |
| 35 | 9.33 | 21 | 60 |

TABLE 5-continued

Biological Test Data for Selected Formula I Compounds

| Ex. No. | Calcium Entry Blockade($pA_2$)[a] | Autolysis (% Protection)[b] | Aggregometry ($EC_{50}$ mg/mL)[c] |
|---|---|---|---|
| 36 | 9.90 | 12 | 40 |
| 37 | 9.89 | 23 | 24 |
| 38 | 8.00 | 16 | 40 |
| 39 | 7.84 | 51 | 128 |
| 40 | 8.44 | 23 | — |
| 41 | 8.56 | — | >128 |
| 42 | 8.08 | — | — |
| 43 | 8.62 | 2 | >32 |
| 44 | 9.03 | 16 | 80 |
| 45 | 9.10 | — | — |
| 46 | 8.25 | 3 | >128 |
| 47 | 9.60 | 21 | 40 |

[a] Calcium blockade as determined in rat dorsal aorta; figures tabulated are $pA_2$ values; $pA_2$ values represent the negative logarithm of the molar concentration of the antagonist which reduces the effect of a dose of agonist to that of half the dose. i.e. a dose ratio of 2. A compound is considered "active" in this screening test if the $pA_2$ value is 7 or greater.
[b] % Protection of high energy phosphate stores in globally ischemic rat myocardium. Values of 20% or more are
[c] In vitro aggregometry (mg/mL) vs collagen as inducing agent. $EC_{50}$ values of 50 mg/mL or less are considered to significantly inhibit aggregation.
[d] Test data unavailable.

What is claimed is:

1. The compound [3-[[2-(1H-indol-3-yl)ethyl]amino]propyl] methyl 1,4-dihydro-2,6-dimethyl-4-(3-nitrophenyl)-3,5-pyridinedicarboxylate.

* * * * *